(12) United States Patent
Doyle

(10) Patent No.: US 12,360,121 B2
(45) Date of Patent: Jul. 15, 2025

(54) ASSAY FOR DETECTION OF AN A2E-SAPOSIN B COMPLEX

(71) Applicant: Syracuse University, Syracuse, NY (US)

(72) Inventor: Robert P. Doyle, Manlius, NY (US)

(73) Assignee: Syracuse University, Syracuse, NY (US)

( * ) Notice: Subject to any disclaimer, the term of this patent is extended or adjusted under 35 U.S.C. 154(b) by 987 days.

(21) Appl. No.: 17/239,961

(22) Filed: Apr. 26, 2021

(65) Prior Publication Data

US 2021/0239715 A1    Aug. 5, 2021

Related U.S. Application Data

(62) Division of application No. 15/793,410, filed on Oct. 25, 2017, now abandoned.

(60) Provisional application No. 62/412,501, filed on Oct. 25, 2016.

(51) Int. Cl.
| | | |
|---|---|---|
| *G01N 33/53* | (2006.01) | |
| *A61K 51/10* | (2006.01) | |
| *G01N 33/68* | (2006.01) | |
| *G01N 33/92* | (2006.01) | |
| *A61B 3/00* | (2006.01) | |

(52) U.S. Cl.
CPC ......... *G01N 33/6893* (2013.01); *A61K 51/10* (2013.01); *G01N 33/92* (2013.01); *A61B 3/00* (2013.01); *G01N 2800/164* (2013.01)

(58) Field of Classification Search
CPC .............. G01N 33/6893; G01N 33/92; G01N 2800/164; A61K 51/10; A61B 3/00
See application file for complete search history.

(56) References Cited

PUBLICATIONS

Huta et al ;ChemMedChem Nov. 2016, 277-282.*
Jin et. al. (J. Clin. Biochem. Nutr.,2008; 42, 167-174).*
Invitrogen Application Note (2008;I retrieved from https://www.thermofisher.com/content/dam/LifeTech/migration/en/filelibrary/pdf/brochures.par.78395.file.dat/o-076281-dynal-apnote.pdf).*
Jin et al., J. Clin. Biochem. Nutr., 43, 95-100, Sep. 2008.*
E. A. Padlan, Adv Prot Chem 49:57-133; 1996.*
Corada et al., Blood, 2001; 97:1679-84.*
Nie, Yan, "The Multi-Substrate Binding Specificity of Saposin B" (Dec. 2016). Dissertations—All. 59.*

* cited by examiner

*Primary Examiner* — Carmencita M Belei
(74) *Attorney, Agent, or Firm* — Wolf, Greenfield & Sacks, P.C.

(57) ABSTRACT

An assay and kit for detecting N-retinylidene-N-retinylethanolamine (A2E) in a sample that uses a lipid binding protein, such as Saposin B, to capture A2E in the sample and assist in the extraction and measurement of A2E via mass spectroscopy. A2E thus serves as a marker for macular degeneration so that the assay and kit of the invention can be used to detect the presence or severity of macular degeneration.

4 Claims, 5 Drawing Sheets

ASSAY FOR DETECTION OF AN A2E-SAPOSIN B COMPLEX

CROSS-REFERENCE TO RELATED APPLICATIONS

The present application is a divisional of U.S. application Ser. No. 15/793,410, filed on Oct. 25, 2017, which claims priority to U.S. Provisional App. No. 62/412,501, filed on Oct. 25, 2016.

BACKGROUND OF THE INVENTION

1. Field of the Invention

The present invention relates to the diagnosis of eye disease and, more specifically, to an assay for detecting toxic eye compounds in urine.

2. Description of the Related Art

The human eye is made up of different tissues that include conjunctiva, cornea, pupil, iris, aqueous humor lens, ciliary body, vitreous humor, retina, choroid, sclera, optic nerve and muscles. The outermost shell of tissue is a layer of transparent membrane called the conjunctiva. It covers a white layer of tissues called the sclera. The cornea is attached to the sclera in front of the eye. Light passes through the cornea into the pupil, which constricts or dilates to control the amount of light that enters the eye. Pupil is in the center of the iris, which is outside of the lens. The change of the size of the pupil is made possible by the ciliary muscles surrounding the pupil. Between the lens and the cornea, there is a kind of liquid called the aqueous humor. Light travels through cornea and pupil, focuses on the lens and then onto the retina, which is a layer of sensitive light-sensing cells. The retina then converts the light signals into electrical signals and passes them onto the visual cortex where the signal is translated into images for the brain to analyze. The macula is the center of the retina. A small depression is present at the center of the macular where the light focuses and forms the clearest vison.

Macular degeneration (MD) is an age related eye disease that is marked by the loss of vision in the center of the eye. It usually happens to older people and is the major cause of vision loss and blindness among them. There are two forms of MD, the dry form and the wet form. The dry form of macular degeneration is an initial, less serious form, and is caused by the gradual loss of photoreceptors of the macula. This photoreceptor loss is thought to arise from the accumulation of intracellular and extracellular material within the eye. Intracellular accumulations, termed lipofuscin, are found within essential support cells called retinal pigmented epithelial (RPE) cells in the macula. The RPE cells are important in that they support the light sensitive photoreceptor cells. The failure of RPE cells leads to death of photoreceptors and a progressive loss of vision. Extracellular accumulations, termed drusen, increase in size and quantity as MD progresses. Lipofuscin mediated RPE cell death is thought to contribute to drusen formation. As drusen accumulates, it can destabilize the macular region by contributing to inflammation, complement activation, and other processes. Over time, dry MD can progress to the more advanced wet form of macular degeneration, also referred to as neovascular macular degeneration. The neovascular macular degeneration occurs when abnormal blood vessels from the vascular layer of the eye enlarges. These blood vessels have the potential rupture, spilling blood and fluid into the retina. Serious complications including blindness can ensue.

Significant lipofuscin that accumulates with age and in certain disorders of RPE cells is the result of disregulation of vitamin A recycling. Major lipofuscin constituents include the di-retinal conjugate N-retinylidene-N-retinylethanolamine (A2E) and its photoisomers, which have adverse effects due to their amphiphillicity and photoreactivity. Excessive lipofuscin accumulation and AMD are considered strongly correlated. Currently, there is no assay available that can detect the presence or severity of macular degeneration. Accordingly, there is a need in the art for an approach that can detect the presence of indicators like A2E and thus detect the presence or severity of macular degeneration.

BRIEF SUMMARY OF THE INVENTION

The present invention is an assay for detecting N-retinylidene-N-retinylethanolamine (A2E) in urine. The lipid binding protein Saposin B is used to capture A2E in a sample, such as a blood or urine sample. The captured A2E may then be extracted from the urine using immunoprecipitation and measured via mass spectroscopy. The present invention thus includes a kit for performing an assay for the diagnosis of macular degeneration, comprising a quantity of a lipid binding protein and an immunoprecipitation substrate having a plurality antibodies to the lipid binding protein. The lipid binding protein may be Saposin B. The immunoprecipitation substrate may comprise protein G beads that have been incubated with antibodies targeting Saposin B. The antibodies may be IgG anti-saposin B antibodies.

The present invention may also comprise a method of diagnosing a subject as having macular degeneration, comprising the steps of obtaining a sample from the subject, adding a quantity of a lipid binding protein to the sample to bind any N-retinylidene-N-retinylethanolamine in the urine, and incubating the urine sample and the quantity of the lipid binding protein with an immunoprecipitation substrate having a plurality of antibodies to the lipid binding protein. The method may also comprise the step of collecting any bound lipid binding protein and N-retinylidene-N-retinylethanolamine. The method may additionally comprise the step of determining how much of any bound lipid binding protein and N-retinylidene-N-retinylethanolamine has been collected. The step of determining how much of any bound lipid binding protein and N-retinylidene-N-retinylethanolamine has been collected may comprise the use of a mass spectrograph

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
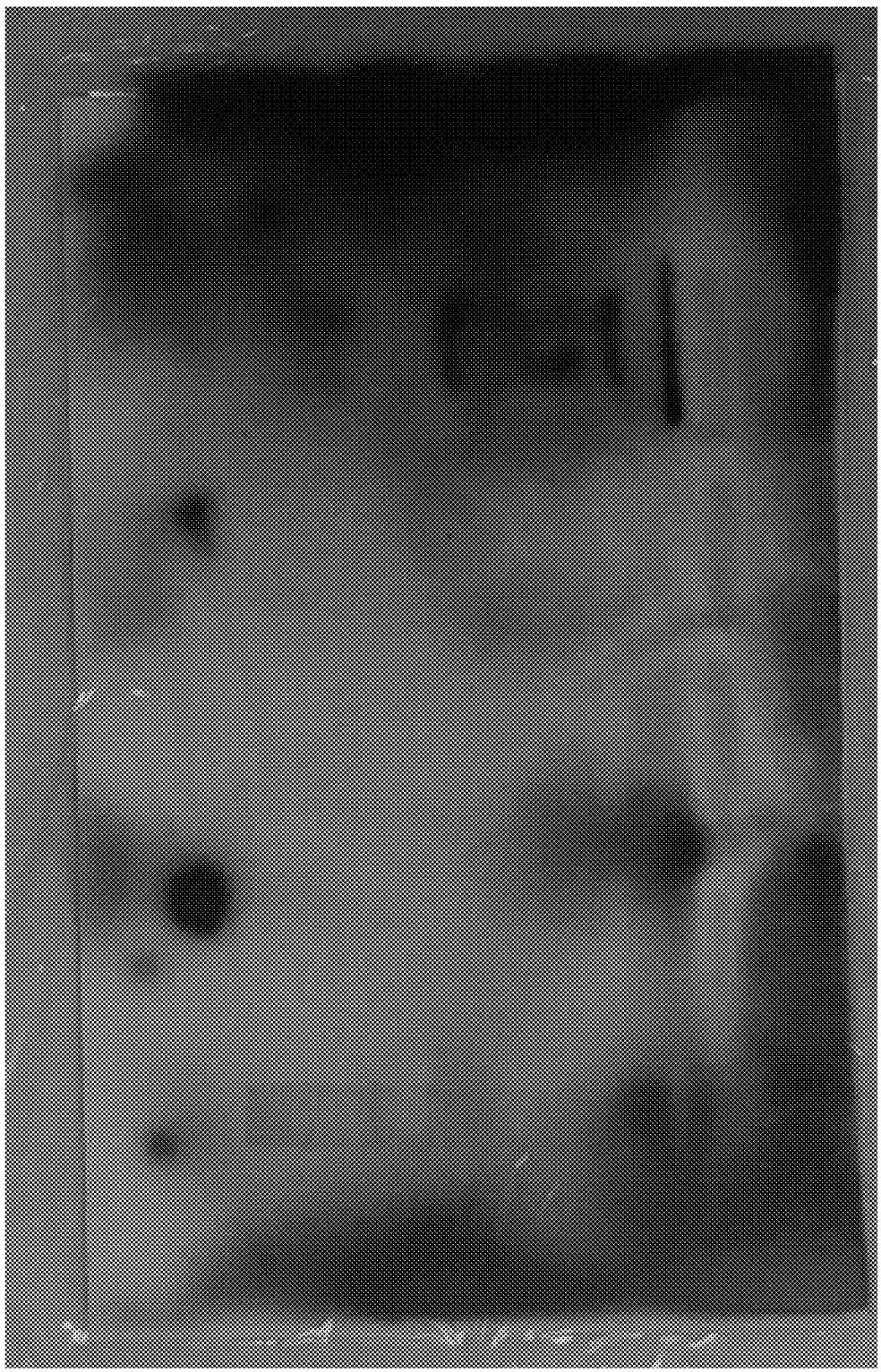

FIG. 4 is a Western blot of SapB from urine, RPE cells, and E. coli expression where the lanes (from left to right) are: Lane 1, Gel Ladder; Lane 2, Saposin B from urine; Lane 3, Retinal Pigment Epithelium cell Saposin B; Lane 4, RPE cell Saposin B; and Lane 5, Saposin B expressed in BL21 *E. coli.*

DETAILED DESCRIPTION OF THE INVENTION

Referring to the figures, wherein like numerals refer to like parts throughout, the present invention comprises an assay that employs saposin B (sapB) to bind A2E in human urine so that is may be detected as measured as an indicator for the presence and severity of macular degeneration. A2E is a compound produced as a part of the light cycle in the human eye and is associated with the development and/or progression of macular degeneration. As A2E builds up in the eye, it is possible it is removed from the body via the blood and then the kidneys in urine, with levels rising in the blood and urine as the disease progresses. Thus, the present invention uses a lipid binding protein, such as Saposin B, to bind A2E, for extraction and measurement.

EXAMPLE

SapB bound A2E was pre-complexed in a 2:1 molar ratio of sapB:A2E in 50 mM phosphate buffer. A volume of this solution was then added to an aliquot of human urine. The sapB-A2E plus urine mixture was then added to magnetic Protein G Beads, which had been incubated with IgG anti-saposin B antibody. After one hour of incubation at 37° C., the sample was magnetized and the excess sample volume was discarded. The sample was then washed with 50 mM phosphate buffered saline solution three times. After each wash, the solution was re-magnetized and the PBS solution was discarded. Following the third wash, mass spectrometry grade methanol was added to the sample and incubated at 4° C. overnight. The sample was then re-magnetized and the MeOH fraction, containing the A2E, was collected for mass spectrometry analysis.

Figure 1A:
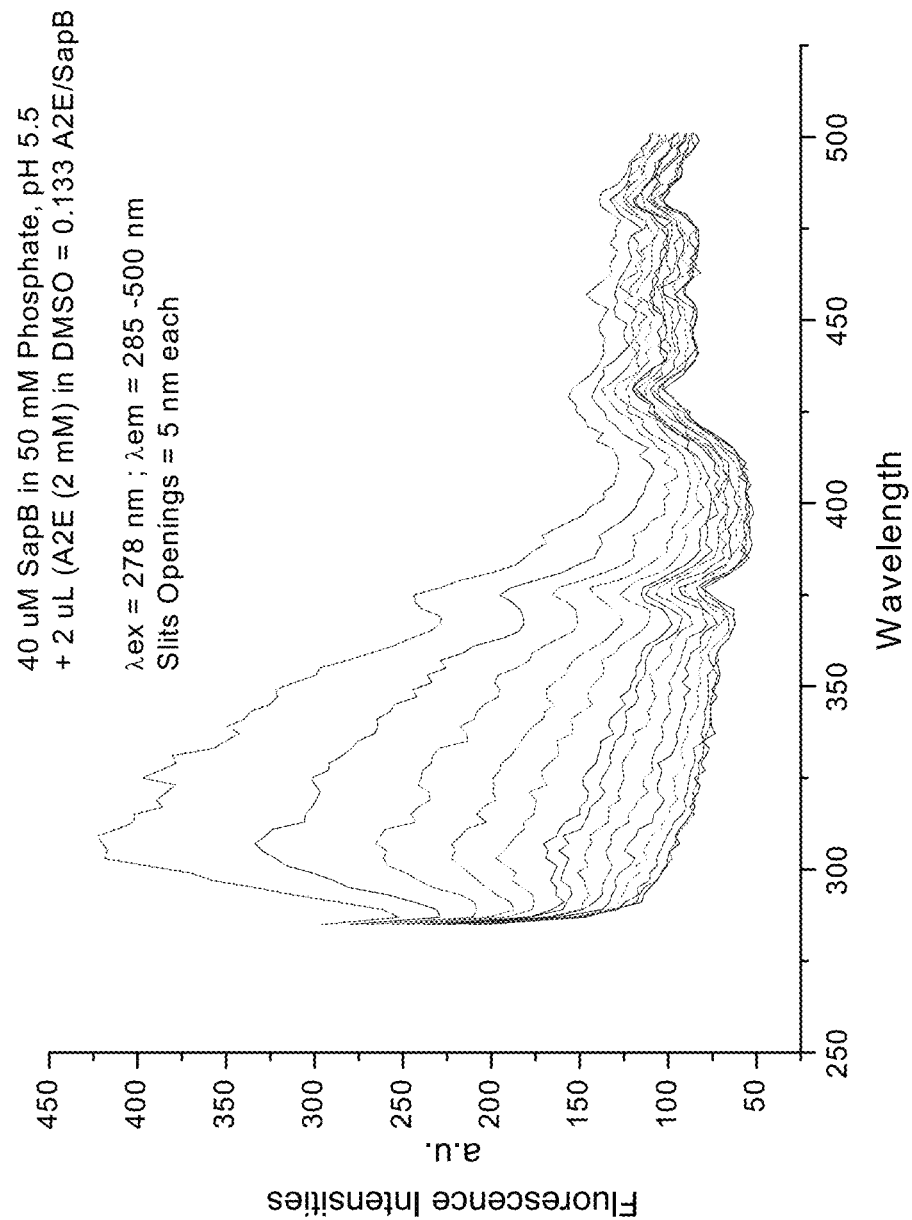
FIG. 1A is a first fluorescence spectroscopy graph showing that Saposin B binds A2E.
Figure 1B:
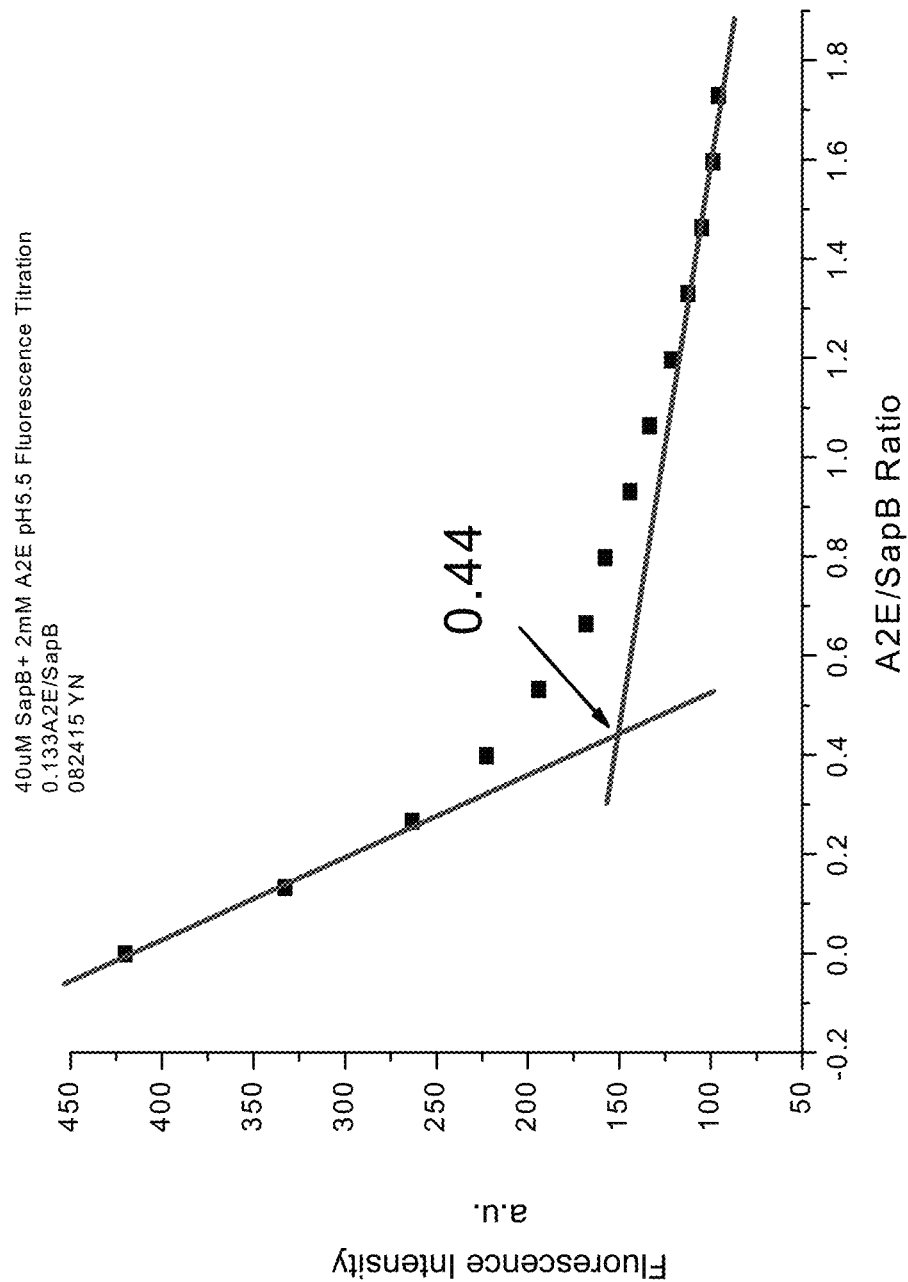
FIG. 1B is a second fluorescence spectroscopy graphs showing that Saposin B binds A2E.
Figure 2:
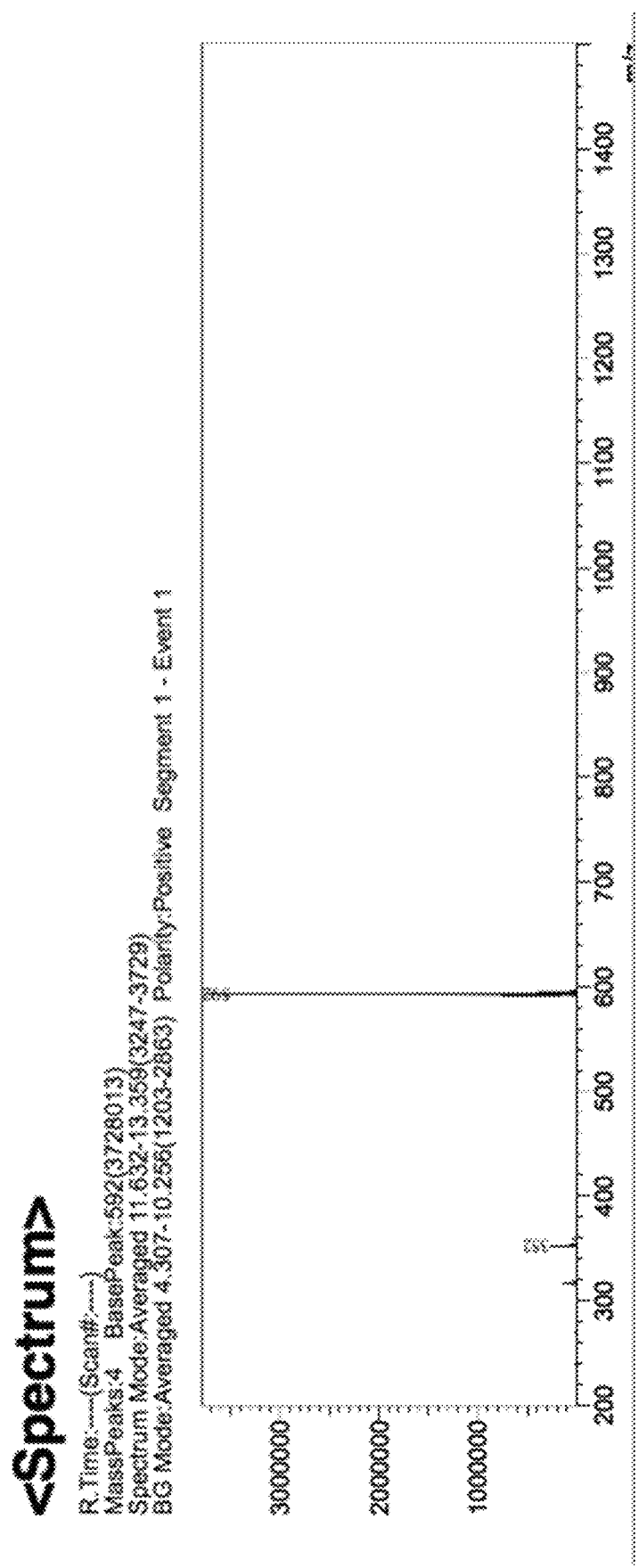
FIG. 2 is a mass spectrum of A2E.
Figure 3:
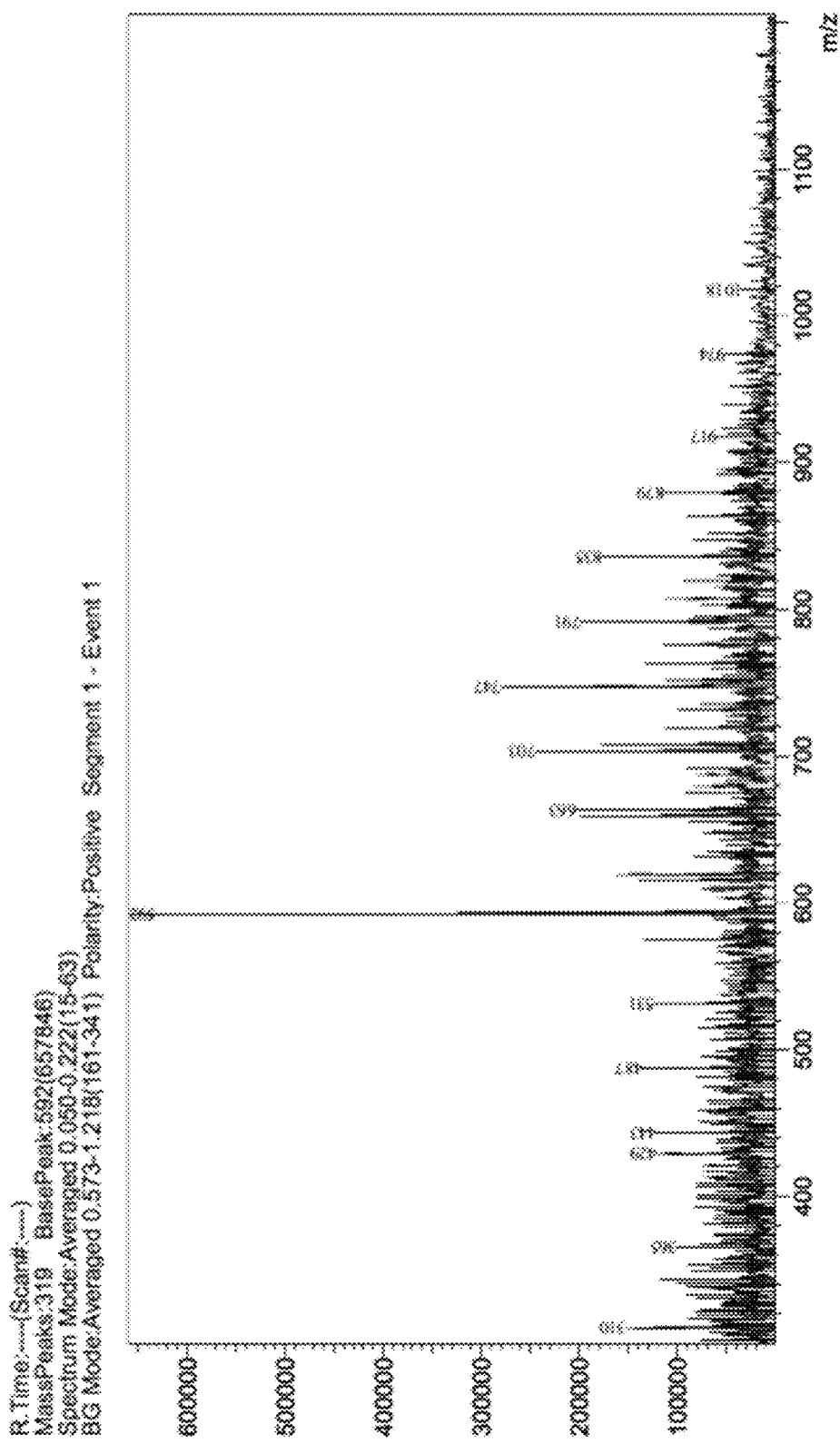
FIG. 3 is a mass spectrum of A2E recovered from SapB-A2E in urine.

FIG. 2 depicts the mass spectrum for pure A2E and FIG. 3 shows the mass spectrum for sapB-A2E recovered from the urine sample. SapB binding to the Protein G Bead-anti SapB complex was confirmed via western blot analysis, as seen in FIG. 4.

The present invention may comprise a kit for the extraction of A2E from a urine sample so that it can be detected and quantified that includes a lipid binding protein, such as Saposin B, that can bind to A2E and enable its extraction. The kit may further include components to assist in the extraction and measurement of A2E. For example, immunoprecipitation substrates, such as protein G beads, that have been incubated with antibodies targeting the Saposin B lipid binding protein, and the associated washing compounds, may be provided in the kit. The present invention thus provides for easy and rapid quantification of a known marker of macular degeneration.

Using A2E levels measured in the blood or urine of healthy patients, patients with diagnosed early stage macular degeneration, patients with advancing and patients with late stage macular degeneration, a relationship between urine levels of A2E and clinical diagnosis can be developed. A classic diseases progression curve or line can thus be generated to enable physicians to track and, in early stage once validated, even diagnose earlier the presence of macular degeneration.

What is claimed is:

1. A method for preparing a N-retinylidene-N-retinylethanolamine (A2E)-saposin B complex in a urine sample for detection of A2E, the method comprising the steps of:
   obtaining a urine sample from a human subject;
   adding a quantity of saposin B to the urine sample to form a A2E-saposin B complex;
   incubating the urine sample with protein G beads that have been incubated with anti-saposin B antibodies to immobilize the A2E-saposin B complex;
   washing the protein G beads comprising the immobilized A2E-saposin B complex; and
   extracting bound A2E from the protein G beads for detection of A2E.

2. The method of claim 1, wherein the antibodies are IgG anti-saposin B antibodies.

3. The method of claim 1, wherein detection is by mass spectroscopy.

4. The method of claim 1, wherein the human subject has macular degeneration.

* * * * *